United States Patent
Scharner et al.

(10) Patent No.: US 6,535,758 B2
(45) Date of Patent: Mar. 18, 2003

(54) METHOD FOR RECORDING AND TRANSMITTING A MULTI-CHANNEL ECG AND AN ARRANGEMENT AS A PORTABLE RECORDER FOR CARRYING OUT THIS PROCEDURE

(75) Inventors: Wilfried Scharner, Aue (DE); Michael Rentzsch, Rheinbach (DE)

(73) Assignee: von Berg Medizingerate GmbH, Zwonitz (DE)

( * ) Notice: Subject to any disclaimer, the term of this patent is extended or adjusted under 35 U.S.C. 154(b) by 0 days.

(21) Appl. No.: 09/789,893

(22) Filed: Feb. 21, 2001

(65) Prior Publication Data

US 2001/0021818 A1 Sep. 13, 2001

(30) Foreign Application Priority Data

Feb. 23, 2000 (DE) .......................... 100 08 411

(51) Int. Cl.[7] ............................................. A61B 5/0432
(52) U.S. Cl. ..................................................... 600/510
(58) Field of Search ............................... 600/510, 509, 600/523

(56) References Cited

U.S. PATENT DOCUMENTS

| | | | | |
|---|---|---|---|---|
| 5,309,920 A | * | 5/1994 | Gallant et al. | |
| 5,417,222 A | | 5/1995 | Dempsey et al. | ........... 128/696 |
| 5,678,562 A | * | 10/1997 | Sellers | |
| 5,730,143 A | * | 3/1998 | Schwarberg | |
| 5,951,485 A | * | 9/1999 | Cyrus et al. | |

FOREIGN PATENT DOCUMENTS

| | | |
|---|---|---|
| DE | 44 41 907 A1 | 6/1995 |
| DE | 197 07 681 C1 | 5/1998 |
| DE | 198 25 898 A1 | 12/1998 |
| DE | 198 48 229 A1 | 6/1999 |
| EP | 0679 041 A2 | 10/1995 |
| WO | WO 99/45841 | 9/1999 |

OTHER PUBLICATIONS

*Diagnose per Handy: Kleines Kästchen sendet EKG per Handy zum Arzt, Krankenhaus Technik*, Apr. 1997, p. 54.

* cited by examiner

*Primary Examiner*—Scott M. Getzow
(74) *Attorney, Agent, or Firm*—Weingarten, Schurgin, Gagnebin & Lebovici LLP

(57) ABSTRACT

Method for recording and transmitting a multi-channel ECG and arrangement as a portable recorder for carrying out the procedure.

The invention concerns a method for recording and transmitting a multi-channel ECG and an arrangement as a portable recorder for carrying out the procedure as part of a telemedical system (ECG—recorder—mobile telephone—evaluation centre).

The purpose of the invention is to enable automatic transmission of the recorded ECG in any length using a conventional, mobile radio controlled telephone.

The invention fulfils this purpose in that following a multi-channel amplification (2) A/D conversion (3) and processing by a pacemaker controller (10) takes place and both are passed on to a microcontroller (4) for further processing and storage with subsequent transmittance via a serial interface (7) to an aforementioned mobile telephone (8) or a PC (9). In addition a removable flash card (6) is also allowed for, by means of which, for example, data can be read in at another location.

11 Claims, 1 Drawing Sheet

METHOD FOR RECORDING AND TRANSMITTING A MULTI-CHANNEL ECG AND AN ARRANGEMENT AS A PORTABLE RECORDER FOR CARRYING OUT THIS PROCEDURE

FIELD OF THE INVENTION

The invention belongs to the field of medical technology and relates the reading, recording and transmittance of bioelectrical signals of the body or parts of the same for diagnostic purposes, in so far as it is a method for recording and transmitting a multi-channel ECG and an arrangement as a portable recorder for carrying out this procedure. This procedure and this arrangement is part of a telemedical system (ECG—recorder—mobile telephone—evaluation center) which forms the basis for a mobile ECG monitoring system for high-risk patients.

BACKGROUND

Equipment for mobile patient monitoring is mainly known in the form of two differing types of devices, and the associated but differing methods.

The first group of devices includes mobile telephones. Representatives of these are, for example, the technical solutions described in patent specifications EP 0 679 041 A2 and DE PS 197 07 681 C1. The technical solution described in patent specification EP 0 679 041 A2 is solely suitable for determining the location of the patient using his positional data. In the case of the technical solution described in the aforementioned patent specification DE PS, the selected medical data is measured by means of special contacts on the mobile telephone which are fifted to the body of the patient or attached by means of wiring and transmitted over the radio communications network, following which immediate aid measures can be taken. Going beyond the simple determination of the position of the patient as described in the aforementioned EP patent specification, here the current data is transmitted immediately, in contrast to the aforementioned EP solution, in order to identify the patient and/or to record the ECG signals. A disclosure of which, that such an aforementioned mobile telephone independently monitors the patient and in a medically significant event automatically transmits the recorded data over the radio communications network, cannot be proven, in particular, but also just because of this reason, cannot be assumed, as an emergency call button on the device which is to be operated by the patient is specified, which the patient himself can or must operate in threatening situations. It must be noted that the disadvantage of these aforementioned technical solutions is that it is not possible to store and record large amounts of relevant data in the case of monitoring measures conducted uninterruptedly over a long period, for several days, weeks or months. An operating facility for transmitting stored and recorded data to a "central" computer for the purpose of evaluating the time course of the relevant data is also not disclosed. Therefore, in the case of the aforementioned solutions, only the data relating to the normal momentary situation or a special momentary event is transmitted, and not the case history leading up to the event and its subsequent evaluation. Furthermore, these radio telephones differ considerably from conventional devices designed for telephoning, as they are special devices employing special application systems and are for the main part scarcely designed or suitable for conventional telephoning purposes.

The second group of devices includes the recorders. Several types of recorders designed to be worn on the body have become known.

So-called long-term ECG recorders generally record the ECG of the patient continuously, usually over a period of 24 hours, by means of an electronic memory. These recorders with integrated data carriers are then given to the doctor. The data is read out or removed and evaluated at a later time. With so-called event recorders a brief ECG period, usually measured in seconds, is recorded and transmitted in the event of a critical heart event or at predefined intervals. This data is transmitted by telephone using a fixed-network telephone in a complicated procedure. The stored ECG is modulated into an audio frequency enabling it to be transmitted by telephone to an evaluation center.

In the case of so-called event recorders with looping function, an ECG is continuously stored by means of electrodes attached to the body and then repeatedly overwritten after a period of seconds or minutes. If an event occurs the case history immediately prior to the event is herewith stored. The ECG is then transmitted to the evaluation center as in the case of the previous event recorders.

Recently recorders that can be implanted have become known. The internal ECG memory allows data to be stored for up to approximately an hour. The ECG can be read out externally.

The particular disadvantageous technical effects of these aforementioned technical solutions with regard to their arrangement and method characteristics are described below.

Long-term ECG recorders only allow the ECG to be analyzed, and therefore pulse irregularities to be detected, after the data has been recorded. The patient is only monitored for 24 or 48 hours, and control results can only be recognized after a further, considerable delay. Consequently only a diagnosis, also termed a "follow-up diagnosis", is possible which—in the case of rare events—offers an extremely limited degree of accuracy and which makes the development, for example in the case of medicinal therapy, practically impossible.

Event recorders are designed to circumvent the disadvantage of the "follow-up diagnosis" to as great an extent as possible. ECG events or phases are recorded. However, these are then transmitted to an evaluation center using a complicated and time-consuming procedure, which inherently leads to a reduction in quality and requires a fixed-network telephone with audio frequency modulation. The entire process is extremely difficult to manage, which severely restricts its use in the age group most at risk, if not making it impossible altogether. Furthermore, a real transmission of data is scarcely possible in an emergency situation. The mobility of the patient is restricted by the required fixed-network telephone. The help of a second person is usually required due to the complicated procedure involved, which is very likely to lead to incorrect use under stressful circumstances. Another factor in the case of the first group of recorders is that a brief event is never recorded as the patient himself must first recognize that an event has occurred, and this is then unavoidably only recorded once it has happened. The diagnostic value is therefore extremely limited.

Although implanted recorders require no effort to be operated, they do need to be implanted and must then be replaced after about 1 year. The implantation of a device for diagnostic purposes can only be expected of a small number of very high-risk patients. The costs of an implantation are, of course, very high. Due to their design, implanted devices are only of limited use as event recorders.

The technical solution as described in patent specification DE OS 198 48 229 A1 describes an arrangement for recording and transmitting digitalized medical data for monitoring a patient online, which comprises a data recording component (A) and a "mobile phone unit" (B) combined in a single device. ECG data is sent directly to the RAM memory by the analog-to-digital converter and then from here directly to the mobile phone unit. This means that it is not possible to treat and/or control data, for example in the sense of data compression, as is evident from the two single figures in the specification, see directions of the arrows for the signal path. The technical function must be questioned in accordance with the contents of the disclosure of the specification, as it is pointless to save the A/D converted signals 0.1 without storing a quantity of data ordered and managed by a controller properly and system-compatibly in order to then process and/or use it further. Furthermore FIG. 1, as well as FIG. 2, of the patent specification DE OS 198 48 229 does not allow the contents of the memory to be read directly into a computer (PC). The characteristics named and claimed in the principle claim of this patent specification DE OS support this evaluation, as the arrangement characteristics named here are supposed to trigger the procedure characteristics ". . . to digitalize the analog recording data from the electrodes in the converter, to store it in the electronic memory, and to transmit it from here from the mobile phone unit over a radio communications network . . . ". In contrast to the facts presented above, a reading out of the memory is described in the specification section in Column 2, Lines 39 to 41, which according to the contents of the disclosure of this specification, however, is not possible with this arrangement. A further disadvantage of the technical solution described in patent specification DE OS 198 48 229 is that only simple pulse rhythm irregularities can be detected using the threshold switches specified here, and that it is not possible to detect critical pulse irregularities, which in turn puts the medical value or the required safety of the patient in question. Finally, it is also a disadvantage that the data acquisition and recording unit, as well as the mobile phone unit, are combined in a single device: it would surely be more practical and also more economical to work with one data acquisition and recording unit and a conventional mobile telephone, rather than possibly having two of the latter, due to the fact that the latter special, and otherwise unusable, mobile phone unit is already included in the technical solution described in patent specification DE OS 198 48 229.

Furthermore, all of this equipment together with the associated procedural processes is not able to record and store ECGs and to transmit them to an evaluation center for immediate processing, generally in computer systems, where necessary with the aid of any commercially available, conventional radio telephone (mobile phone).

SUMMARY OF THE INVENTION

Taking into consideration the shortcomings of the state of the art described above and their causes, this invention is based on the purpose of creating a method and an arrangement with which recorded ECGs can be transmitted automatically in any length, as well as triggering an automatic transmission of ECG data in the event of critical pulse irregularities using a (commercially available) conventional mobile telephone, and thereby forming an "ECG transmission" complex exploiting the full potential of mobile telephones. A further purpose of the invention should also be to realize such a high memory capacity so that the arrangement allows either discontinuous ECG monitoring over a longer period of days, weeks to months, or continuous ECG monitoring over 48 hours, whereby removal of the storage medium should also be possible. Total mobility of the patient when recording ECGs and during data transmission should also be ensured. This purpose is fulfilled for a generic method and a generic arrangement according to the present invention by the features listed in the characterizing part of the claims 1 to 8.

An arrangement is hereby created which is represented by a portable recorder with the following principal modules: multi-channel amplifier, A/D converter, microcontroller, RAM and flash-ROM memory elements, a removable flash card, pacemaker controller and interface. A mobile telephone unit was intentionally not included in the arrangement according to the invention, as this involves an associated unusable performance in partially restricting special functionality. It was also the aim of the invention to implement according to the present invention universal and commercially available mobile telephones (mobiles), as have already been sold millions of times over, for data communication. Previously known, modern and recent technology for mobile patient monitoring did not take this, economically, very important factor into consideration and always assumed that it would be able to integrate mobile radio telephone technology into such a medical monitoring system in a converted form for its own purposes. The advantages of separating data acquisition and recording from the mobile phone unit are obvious. In addition to simpler assembly and lower work, time, material and cost expenditure during manufacture, marketing and operation (particularly with regard to the weight in the latter case), as otherwise devices would be "doubled", any type of mobile phone (which is often available anyway) can be used. This technical solution will, of course, always be represented with a mobile telephone according to the present invention. The recorder modules allow data communication with the mobile telephone in such a way that a predefined telephone call is made when the mobile phone is so instructed by the recorder arrangement in order to be able to use it to transmit ECG data with the patient's data using a suitable data protocol, as well as a data and transmission backup. Only by means of the arrangement or data processing of the, or by the, microcontroller in the signal or data form differing to the nearest knowledge and technology (DE OS 198 48 229) according to the main characteristics of the invention, and by means of a special data protocol, is it possible to carry out a multi-channel ECG transmission by means of data compression of the individual channels, which also results in shorter transmission times. The aforementioned nearest knowledge and technology is not aware of this resource-effect relationship. Here ECG data is sent from the A/D converter directly to the RAM memory and in turn from here directly to the mobile phone unit. As a result, a data-compressing treatment/control of this data is not possible. Compared to the arrangement of the aforementioned nearest knowledge and technology, this invention produces advantageous effects of such proportions that in the case of the solution in accordance with the invention as described here data is compressed by the microcontroller before it is sent to the mobile phone, which reduces the transmission time approximately by a factor of 5 compared to non-compressed transmission, and that according to this technical theory in accordance with the invention a theoretically unlimited number of individual ECG channels can be transmitted, even if the data quantities in the individual channels differ from one another due to the various degrees of compression which are possible. In contrast to the nearest knowledge and technology, this technical theory uses in accordance with the invention a memory card employing flash technology (flash card) for recording data. This method of storage also allows data to be stored for 24 or 48 hours when used in conjunction with transmission by telephone, or it permits the storage of a very large number of short-term individual events. It is therefore also possible in a second mode to "Store Only" the short or long-term ECG, thereby creating a new operating mode for the long-term ECG and event recording methods. Furthermore the technical theory enables the permanent storage of data using a flash card even when the battery is changed or its power reserves are absolutely exhausted. This allows recorded data to be transmitted over a mobile phone at any time in the future, and no data loss occurs even when the battery is changed in the meantime. Finally, the flash card with the stored data employed in accordance with the invention can be removed from the recorder and read into a PC at another location. This expands the application possibilities when storing large quantities of data. It is not absolutely necessary to read out data via the serial interface. The technical solution in accordance with the invention therefore has the advantage of 3 methods, namely:

- event recording in loop mode, including storage of the case history with the option of being able to transmit data immediately via mobile phone in case of emergency,
- event storage for subsequent evaluation, as well as
- complete, continuous long-term ECG storage over a period of several days. To record an event it is only necessary to trigger recording by pressing one key; the following processes take place fully automatically.

Transmittance of ECG data in the event of critical pulse irregularities takes place automatically and safely by means of a special software. The threshold switches as specified in the current knowledge and technology are only able to detect simple pulse rhythm irregularities, which puts the medical value or the required safety of the patient in question.

BRIEF DESCRIPTION OF THE DRAWINGS

The invention is briefly described here in more detail using the sample model shown in FIG. 1.

DETAILED DESCRIPTION OF THE PREFERRED EMBODIMENTS

Figure 1:
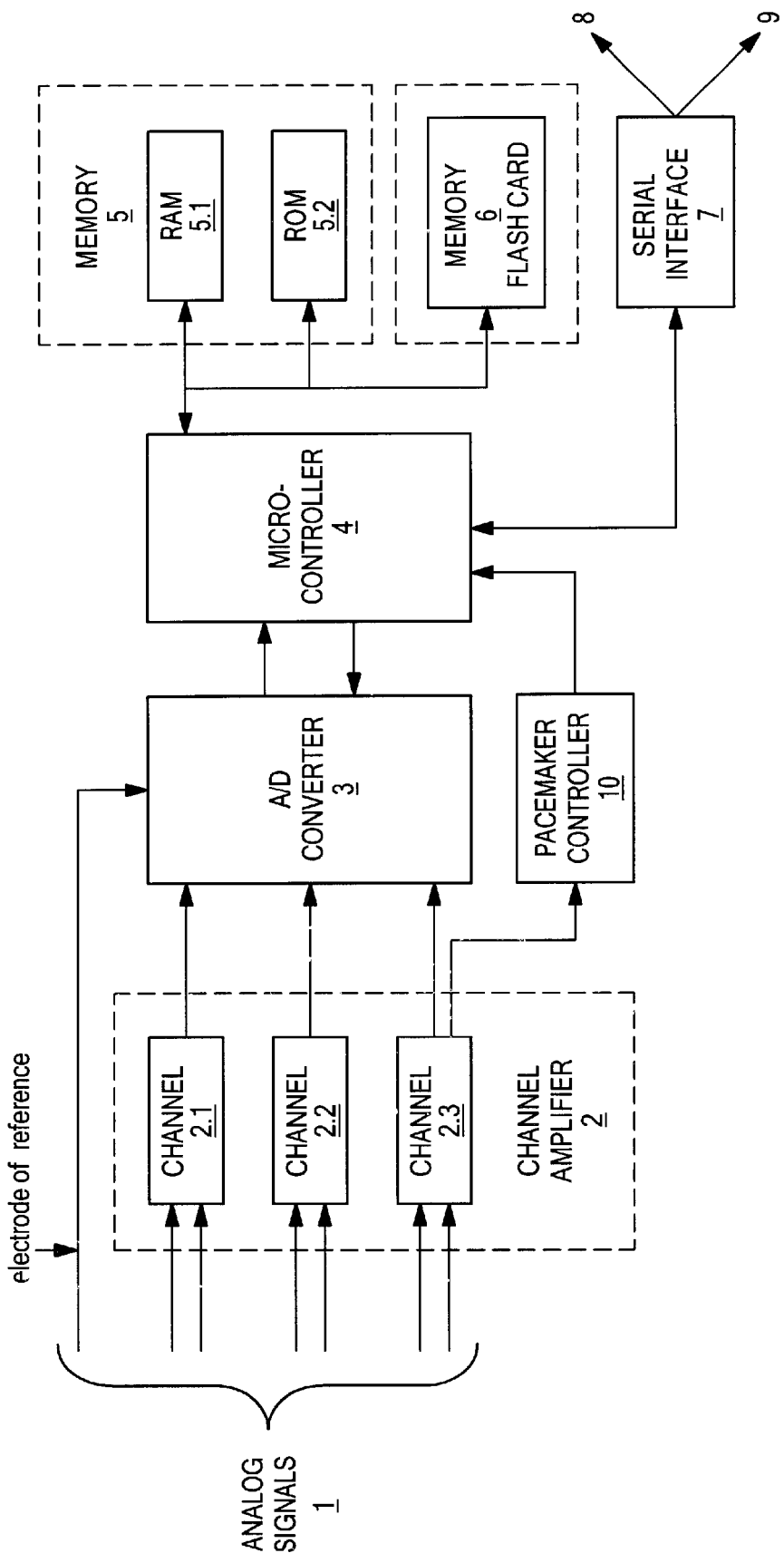

FIG. 1 shows the block diagram, as can be used to illustrate the invention. Three ECG signals are fed from the recorded analog signals 1 to a three-channel amplifier 2 with its three channels 2.1, 2.2 and 2.3. The digitalized signals from the three channels 2.1, 2.2 and 2.3 are fed to the microprocessor 4, which for its part can influence the A/D converter 3 if required and necessary. A data line to the pacemaker controller 10 is also switched from one ECG channel, e.g. Channel 2.3, which detects the pacemaker impulse during a pacemaker ECG and marks the ECG at the detected time and feeds it to the microcontroller 4. Processed data is stored according to its further purpose in the memory arrangements 5 and 6 assigned in parallel to the microprocessor 4, from where it is retrieved by the microcontroller 4 as required and can be further or re-processed if necessary. The flash card 6 is designed to be removed from the recorder arrangement, so that the data stored on the card can be read into a PC at another location where it can then be processed and evaluated. This expands the application possibilities when storing large quantities of data. It is not absolutely necessary to read out data via the serial interface. The planned serial interface 7 connected to the microcontroller 4 transfers the data either to a PC 9 or the commercially available mobile telephone 8. Signal flow in the opposite direction from the mobile telephone 8 or the PC 9 to the microcontroller 4 is also possible if required.

The recorder is configured with patient and transmission data via the serial interface before the ECG monitor is put into operation.

At the evaluation center the patient is decoded and the ECG is assigned in the database. This ensures an absolutely fail-safe identification. A received ECG is indicated so that an immediate evaluation is possible and the appropriate action can be initiated, e.g. the patient can be called using the mobile telephone or the emergency medical service can be alarmed. If transmittance of the ECG cannot be assured due to inadequate radio transmission conditions, the call is repeated. Should transmission still not take place, the stored ECG is transmitted together with the next event.

What is claimed is:

1. Method for recording and transmitting a multi-channel ECG as part of a telemedical system (recorder—transmission element—evaluation center) in which the patient's medical data is permanently recorded, digitalized, stored and transmitted by radio signal to an evaluation center by means of a mobile arrangement worn on the body of the patient (recorder) for approximately simultaneous evaluation or monitoring;

characterized in that following the recording of the ECG the signals are prepared by means of a multi-channel amplifier and a connected A/D converter, that these signals are prepared accordingly and fed from the multi-channel amplifier to a microcontroller for processing, which queries the A/D converter, that the data processed by the microcontroller is stored in a memory combination and time-related on a flash card, whereby here a flow-back of data from the memory elements and to the microcontroller is also allowed for, that the microcontroller controls the serial interface for the recorder configuration and the reading out of the processed ECG by means of a special software in such a manner that, firstly, data can be transmitted to a mobile telephone (Mobile Telephone mode) and, secondly, data can be read out directly to the computer (PC Communication mode), that one of the ECG signals emitted from the multi-channel amplifier is fed to a pacemaker controller, which during ECG signal detects the pacemaker impulse, marks the ECG at the detected time and feeds it to the microcontroller.

2. Method described in claim 1, characterized in that following transmission/storage of the multi-channel ECG at an evaluation center, the evaluation of this ECG can take place using known evaluation programs.

3. Method described in claim 2, characterized in that event recording and continuous long-term monitoring can be carried out using the same method according to the aforementioned method characteristics and the same arrangement.

4. Method described in claim 1, characterized in that a permanent monitoring of critical pulse irregularities, which require an immediate evaluation, takes place in the microcontroller of the recorder arrangement by means of a special artifact-safe software and that following detection of such an irregularity the current ECG, as well as the ECG prior to this irregularity, are automatically transmitted in the Mobile Telephone mode to the evaluation center where the appropriate medical measures can be initiated.

5. Method described in claim 4, characterized in that event recording and continuous long-term monitoring can be carried out using the same method according to the aforementioned method characteristics and the same arrangement.

6. Method described in claim 1, characterized in that the mobile telephone is automatically switched on and the stored call number of the evaluation center is automatically dialed with the aid of a special software in the Mobile Telephone mode after an event has occurred.

7. Method described in claim 6, characterized in that event recording and continuous long-term monitoring can be carried out using the same method according to the aforementioned method characteristics and the same arrangement.

8. Method described in claim 1, characterized in that event recording and continuous long-term monitoring can be carried out using the same method according to the aforementioned method characteristics and the same arrangement.

9. A portable recorder for carrying out the method of claim 1, comprising an A/D converter unit, a memory unit, a microcontroller characterized in that the ECG signals are switched to a multi-channel amplifier with the channels (2.1), (2.2), (2.3), . . . (2.X), whereby one or more of the signals can accumulate at a A/D converter arranged after the amplifier, that the A/D converter and a pacemaker controller, arranged in parallel to one another, are connected in series to the amplifier, whereby these in turn are jointly applied to a microcontroller, wherein the microcontroller transmits A/D converting parameters to and directs the operation of the A/D converter, wherein the microcontroller directs the transmitting of data between the memory unit, a flash card, and a serial interface, and wherein the microcontroller directs the memory unit, the flash card, and the serial interface, whereby the serial interface provides access to the mobile telephone and/or the computer.

10. Arrangement described in claim 9, characterized in that the memory combination is composed of at least one RAM and one flash ROM.

11. Arrangement described in claim 9, characterized in that the flash card is not permanently installed in the recorder arrangement, but that it is designed to be removed.

* * * * *

UNITED STATES PATENT AND TRADEMARK OFFICE
CERTIFICATE OF CORRECTION

PATENT NO.     : 6,535,758 B2
DATED          : March 18, 2003
INVENTOR(S)    : Wilfried Scharner et al.

It is certified that error appears in the above-identified patent and that said Letters Patent is hereby corrected as shown below:

Column 1,
Line 33, "fifted" should read -- fitted --.

Signed and Sealed this

Ninth Day of March, 2004

JON W. DUDAS
*Acting Director of the United States Patent and Trademark Office*